United States Patent
Wang et al.

(10) Patent No.: US 7,054,008 B2
(45) Date of Patent: May 30, 2006

(54) METHOD AND APPARATUS FOR ELEMENTAL AND ISOTOPE MEASUREMENTS AND DIAGNOSTICS-MICROWAVE INDUCED PLASMA-CAVITY RING-DOWN SPECTROSCOPY

(75) Inventors: Chuji Wang, Starkville, MS (US); Christopher Winstead, Hattiesburg, MS (US); Yixiang Duan, Los Alamos, NM (US)

(73) Assignee: Mississippi State University, Mississippi State, MS (US)

( * ) Notice: Subject to any disclaimer, the term of this patent is extended or adjusted under 35 U.S.C. 154(b) by 207 days.

(21) Appl. No.: 10/367,806

(22) Filed: Feb. 19, 2003

(65) Prior Publication Data

US 2004/0160605 A1    Aug. 19, 2004

(51) Int. Cl.
*G01N 21/01* (2006.01)
*G01N 21/61* (2006.01)

(52) U.S. Cl. .................................. 356/437; 356/316

(58) Field of Classification Search .............. 356/316, 356/437
See application file for complete search history.

(56) References Cited

U.S. PATENT DOCUMENTS

| | | | | |
|---|---|---|---|---|
| 4,955,717 A * | 9/1990 | Henderson | ............. | 356/316 |
| 5,062,708 A * | 11/1991 | Liang et al. | ............. | 356/316 |
| 5,671,045 A * | 9/1997 | Woskov et al. | ............. | 356/316 |
| 5,903,358 A * | 5/1999 | Zare et al. | ............. | 356/437 |
| 5,912,740 A * | 6/1999 | Zare et al. | ............. | 356/437 |
| 6,421,127 B1 * | 7/2002 | McAndrew et al. | ......... | 356/437 |
| 6,727,492 B1 * | 4/2004 | Ye et al. | ............. | 250/227.18 |
| 6,795,190 B1 * | 9/2004 | Paul et al. | ............. | 356/437 |

OTHER PUBLICATIONS

Birza et al, "Cw cavitiy ring down spectroscopy in a pulsed planar plasma expansion", Chemical Physics 283 (2002) pp. 119-124.*

* cited by examiner

*Primary Examiner*—Richard A. Rosenberger
(74) *Attorney, Agent, or Firm*—DLA Piper Rudnick Gray Cary US LLP

(57) ABSTRACT

Provided is a novel system for conducting elemental measurements using cavity ring-down spectroscopy (CRDS). The present invention provides sensitivity thousands of times improved over conventional devices and does so with the advantages of low power, low plasma flow rate, and the ability being sustained with various gases.

17 Claims, 10 Drawing Sheets

METHOD AND APPARATUS FOR ELEMENTAL AND ISOTOPE MEASUREMENTS AND DIAGNOSTICS-MICROWAVE INDUCED PLASMA-CAVITY RING-DOWN SPECTROSCOPY

This invention was made with U.S. Government support from the United States Department of Energy through Environmental Management Science Program Grant Number DE-FG07-02ER63515 in Mississippi State University and Grant Number 86680 in Los Alamos National Laboratory.

FIELD OF THE INVENTION

The present invention relates to a novel system for providing a sensitive technique for elemental measurements using cavity ring-down spectroscopy (CRDS) combined with a compact microwave plasma source as an atomic absorption cell. More particularly the system of the present invention combines the high sensitivity of CRDS with a low power microwave plasma source to provide a novel instrument that gives high sensitivity and capability for elemental and hyperfine structure measurements. CRDS, which uses a single laser pulse ringing down inside the cavity over a thousand times, provides several orders of magnitude more sensitive than conventional absorption techniques. Additional benefit is gained from a compact microwave plasma source that possesses advantages of low power and low plasma gas flow rate, which benefit for atomic absorption measurement.

BACKGROUND OF THE INVENTION

Inductively coupled plasma (ICP) sources have been widely used in atomic emission spectrometry and mass spectrometry [1–2]. Most work in atomic absorption spectrometry (AAS) utilizes flames and electrothermal devices as atomizers for AAS measurement [3,4], although the use of plasma sources as atomization cells for AAS measurement was proposed in the early development stage of plasma spectrometry. In the first report, a multiple beam system for ICP-AAS measurement was described that used a hollow cathode lamp as a radiation source and an ICP as an atomization cell [5]. A later work reported detection limits for ICP-AAS for determination of Ag, Al, Ca, Cu, Mo, Ta and V at about ppm levels using a short plasma torch as an absorption cell [6]. Based on theoretical considerations and calculations, Magyar, et al., suggested ICP might not be an ideal source for AAS measurement [7]. The following reasons were identified: 1) high plasma gas flow rate required for maintaining the ICP dilutes the concentration of analyte atoms, resulting in a short residence time of analyte in the plasma; 2) absorption path length in an ICP is relatively short, and not beneficial for AAS measurement; and 3) high temperatures in the ICP source favor the production of excited and ionized species while AAS needs ground level populations. Therefore, subsequent research on ICP-AAS has mainly focused on fundamental studies and plasma diagnostics [8–10].

Although CRDS has rapidly gained popularity in the molecular spectroscopy community, there are few reports exploring atomic absorption with CRDS [11–13]. Thus far, the only published research has used inductively coupled plasma as an atomization cell for CRDS measurement [11–12]. This exploratory research showed very promising results to adapt CRDS for atomic absorption measurement in plasma sources. However, using a conventional ICP as an atomization cell for AAS measurement has some obvious limitations [7]. It is widely believed in the art that the ICP can be a poor source for ground state neutral species because most of the analyte atoms are either excited or ionized at conventional ICP's. With such knowledge in mind, most recent work on ICP-CRDS has lowered the ICP power in combination with a modification to the ICP torch design so that ground state populations of analytes can be significantly enhanced, allowing improved detection limits to be achieved using cavity ring-down spectroscopy [12]. However, a lowered operating power makes the ICP plasma source less robust or even fragile.

Microwave induced plasma (MIP) is a powerful alternative source for elemental determination and has been extensively used in analytical atomic spectrometry [14]. Compared with other types of plasma sources, the MIP offers some attractive characteristics, such as its unique features of high excitation efficiency for metal and nonmetal elements; capability of working with various gases; simplicity; and low cost for instrumentation and maintenance. In addition, microwave plasmas can be sustained at fairly low power and low gas flow rate, making them a desirable source for absorption measurement [15]. There have been publications reporting the use of microwave plasma sources as atomization cells for conventional AAS measurement with hollow cathode lamps (Hcl) [16–19] to pursue sensitivity, including designing high efficiency desolvation devices to remove water vapor loading [18], designing various plasma discharges for better absorption measurement [15], adapting different sampling device [17], and regulating the plasma gas flow system. With conventional lamps as light source, MIP-AAS gives about two to three orders of magnitude better results than ICP-AAS does [15].

In spite of some minor advances made in various related technologies in recent years, it remains the rule that the limitations of conventional elemental and isotope measurement and diagnosis is still bound by obvious sensitivity limitations.

By the present invention, these long-standing limitations have been addressed to provide a system that gives high sensitivity and capability for elemental and hyperfine structure measurements.

SUMMARY OF THE INVENTION

The inventors in developing the system of the present invention surprisingly discovered that a microwave plasma source could be successfully combined with cavity ring-down measurement to provide the sensitivity and capability of measurement that have previously not been possible. The system developed by the inventors takes the advantages of CRDS extremely sensitive absorption measurement and combines them with the microwave plasma source of low power, low gas flow rate, and ease of operation. In the present invention, the two diverse technologies have been combined in a complementary manner so as to provide the surprising result of a novel instrument that has the capability of a microwave plasma source for cavity ring-down measurement.

DETAILED DESCRIPTION OF THE INVENTION

The following description of the present invention is illustrative of the inventor's discovery and is not intended to limit the scope of the invention, which is defined by the claims appended hereto.

A laboratory CRDS system that includes a tunable dye laser is used to demonstrate the concept of the present invention. It is also within the concept of the present invention to use continuous wave diode lasers or other suitable sources of laser energy. The inventors have proven their novel concept by testing and building a science base that demonstrates the operability of the system, its novel instrument and method for use thereof. A laboratory designed and built sampling system for solution sample introduction was used for the new instrument testing. The ring-down signals were monitored using a photomultiplier tube (PMT) and recorded using a digital oscilloscope interfaced to a computer. It is also within the concept of the present invention that ring-down signals can be monitored using photodiode detectors or any other monitoring means known in the art. Lead is chosen as a typical element for the system optimization and characterization. Baseline noise of the plasma source has been thoroughly studied in this work. A detection limit of 0.8 ppb ($10^{-10}$) is obtained with the device.

EXAMPLES

Instrument Assembly and Setup

Figure 1:
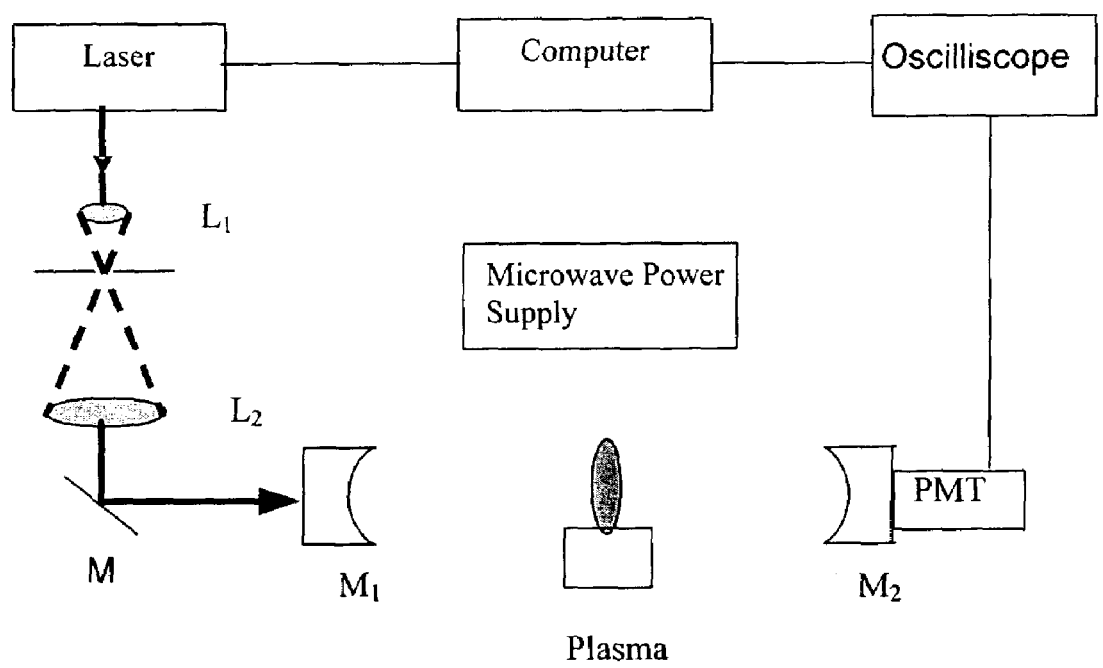
FIG. 1 is a schematic diagram of the system setup of the present invention. L1, L2 are lens, M is a reflected mirror, M1 and M2 are cavity mirrors, PMT is photomultiplier tube.

A schematic diagram of the operational system setup for the present invention is shown in FIG. 1. The system consists of five primary parts: a laser source, a plasma source, ring-down cavity, sampling device, and detection electronics. The optical configuration in this embodiment of the present invention is similar to the assembly reported in the literature [12]. Tunable ultraviolet laser beam is generated using a narrow linewidth, dual grating dye laser (Radiant NarrowScan) followed by frequency doubling (Inrad Autotracker III). A 20 hertz repetition rate Nd:YAG laser (Continuum Powerlite 8020) is used to pump the dye laser. The minimum scanning step of the dye laser is 0.0003 nm, with a line width of about 0.08 $cm^{-1}$ at 283.3 nm. A spatial filter system consisting of two focusing lenses and a pinhole is used for mode matching the laser beam to the ringdown cavity. The first lens is used to focus laser beam onto a pinhole of 25 mm diameter and the second lens couples the filtered beam from the pinhole into the cavity. With this optical configuration, a Pseudo-Gaussian beam is generated for ring-down measurement. Two plano-concave mirrors with a 6 meter radius of curvature (Los Gatos Research) is used to form a 770 mm cavity. The maximum reflectivity of the mirrors at 283.3 nm is 99.85%. The ringdown signal is monitored using a photomultiplier tube (PMT-Hamamatsu R928) and recorded using a digital oscilloscope (Tektronix, TDS 410A) interfaced to a computer. A 10 nm bandpass interference filter (CVI Laser) is mounted in the front of the PMT to reject emissions from the plasma system. A pulse generator (Stanford Research Systems DG 535) controls the system timing. A 0.5 meter monochromator (ARC Spectra-Pro-500), coupled with a CCD array (Spectrum One CCD-200) is used for simultaneous monitoring emission spectrum.

Microwave Plasma Source

In this embodiment of the present invention a robust microwave plasma source known as microwave plasma torch was used as an atomization cell for ring-down measurement. The plasma takes a toroidal shape and can be operated with a power ranging from tenths watts to several hundred watts or as high as 1,000 watts, preferably between 50 to 1,000 watts. The plasma source used here is the same as was used in our earlier research for atomic emission measurement [20]. The flame-like plasma formed by the torch has been demonstrated to be an excellent stable source for atomic spectrometry [21–22]. The plasma torch, consisting of three coaxial tubes, offers some additional advantages over conventional microwave plasma sources, and has been widely applied in emission, mass spectrometry, and fluorescence measurement [14]. The torch is connected to a 2450 MHz microwave power supply through 1-m coaxial cable. The plasma source is mounted inside the optical cavity on a X-Y-Z three-dimensional adjustable stage for precise alignment of optical beams for maximum absorption. Typical operational parameters for the instrument are summarized in Table 1.

TABLE 1

Operational conditions of the instrument

Plasma

| | |
|---|---|
| Microwave power | 120 W |
| Plasma supporting gas flow rate | 0.35 L/min |
| Plasma central gas flow rate | 0.45 L/min |

TABLE 1-continued

Operational conditions of the instrument

Sampling

| | |
|---|---|
| Sample up-take Rate | 0.75 ml/min |
| Heating temperature of the ultrasonic nebulizer chamber | 140° C. |
| Cooling temperature of the ultrasonic nebulizer desolvator | −5° C. |
| Heating temperature of the membrane device | 80° C. |
| $N_2$ gas flow rate in the drier | 0.5 L/min |
| Sample concentration | 100 ng/ml |

Optical set-up

| | |
|---|---|
| Laser frequency | 20 Hz |
| Scanning step | 0.0003 nm |
| Reflectivity of cavity mirrors | 99.8% |
| Filter bandpass | 10 nm |

Data acquisition

| | |
|---|---|
| Number of laser pulse for average | 20 |

Sampling Device

Samples can be delivered through a commercial peristaltic pump into an ultrasonic nebulizer (U-5000 AT+, CETAC), where the liquid samples are generated into fine, wet aerosols through an ultrasonic transducer. It is recognized that any other suitable delivery system can be employed without departing from the concept of this invention. The heating temperature inside the ultrasonic nebulizer is about 140° C., with a cooling chiller operating around −5° C. at the aerosol outlet. The aerosol generation efficiency by the system is about 7–10% with a sample uptake rate of 0.75 ml/min. An additional desolvation device is built and applied to further control the solvent loading in the low power plasma source and to enhance the system performance. The desolvation device consists of a membrane desolvator and a nitrogen gas stream. A flow rate of about 0.5 L min$^{-1}$ nitrogen is introduced into the space between the desolvation chamber and the membrane tube to remove the water vapor produced during the desolvation process. With this arrangement, a good desolvation efficiency is obtained and the plasma source can run fairly stable with heavy aerosol loading.

Chemicals and Reagents

High purity argon (99.999%) was used as working gas for supporting the plasma source although it is within the concept of the invention to employ any gas known in the art to be suitable for such purpose. Sample solutions were prepared by diluting standard solutions (1000 μg/ml, Absolute Standard Inc, Hamden, Conn.) and introduced into the plasma source through the sampling system.

Results

Measurement Principle of Plasma Source CRDS

O'Keefe and Deacon first developed the cavity ring-down spectroscopy (CRDS) in 1988 [23]. The technology is based upon a significantly different principle from traditional absorption spectroscopy methods. In CRDS, absorption is measured via a change in the decay time for light trapped in an optical cavity rather than a change in intensity. Absolute absorption can be readily determined using CRDS and the performance of the technique is relatively unaffected by fluctuation noise of the laser source. Although experimental methods and applications of CRDS have experienced rapid growth since the earliest work therein, and numerous variations on the technique have been reported, the basic operating principle remains the same. A laser beam is injected through one end mirror of the cavity where it remains trapped between the mirror surfaces. The intensity of the light in the cavity decays exponentially with time at a rate determined by the round trip losses experienced by the laser pulse. These losses are typically due to the finite reflectivity of the cavity mirrors, optical absorption, and scattering. The decay behavior can be monitored by a photomultiplier tube (PMT) located behind the second mirror. In the simple case of a low-pressure gas uniformly filling the cavity, the cavity loss originates predominantly from the mirrors and absorption of the sample based on the Beer-Lambert law. The time constant of the exponential decay or ring-down lifetime is given by:

$$\tau = \frac{d}{c(1 - R + \sigma(v)nd)} \quad (1)$$

where, c is the speed of light, d is the cavity length, R is the reflectivity of the cavity mirrors, n is the sample density, and σ(v) is absorption cross-section at laser frequency v. The term σ(v)nd represents the single-pass absorbance of the sample in the cavity and is recognized as the exponent from the Beer-Lambert law. From equation (1), two clear advantages of CRDS are evident. First, determining the ring-down time constant allows for an absolute absorbance measurement without relative light intensities. Secondly, excellent absorbance detection limits at a few parts-per-million fractional absorbance can be easily obtained with high reflectivity mirrors.

The development of the CRDS technique provides a unique opportunity for highly sensitive atomic absorption measurements. With a plasma source as an atomization cell, the absorption sample only fills a fraction of the cavity length. Additional losses are introduced due to scattering from the plasma region and the air in the open cavity. However, in practice, such scattering can be simply incorporated by substituting a lower effective reflectivity $R_{eff}$ for R in equation (1). This effective reflectivity is determined by measuring the ring-down time without an analyte present (blank). Experimentally, the direct measurements are the ring-down lifetimes τ and $\tau_0$ with and without an analyte in the injected solutions. Thus, the absorbance can be rewritten as:

$$\text{absorbance} = \frac{d}{c}\left(\frac{1}{\tau} - \frac{1}{\tau_0}\right) \quad (2)$$

Optimization of the System Parameters

In this work, the optimization work has been performed based on simplex method, in which only one parameter was varied and examined at a time when all other parameters were fixed. In order to find relative optimum conditions for each parameter, a pre-examination was performed to determine the values that are proper as base for further examination. All major parameters, including microwave power influence, carrier gas flow rate, plasma gas flow rate, and observation height were optimized before any further exploration. For comparison purpose with ICP plasma source in our previous work, lead was deliberately chosen for this optimization work and performance evaluation.

Figure 2:
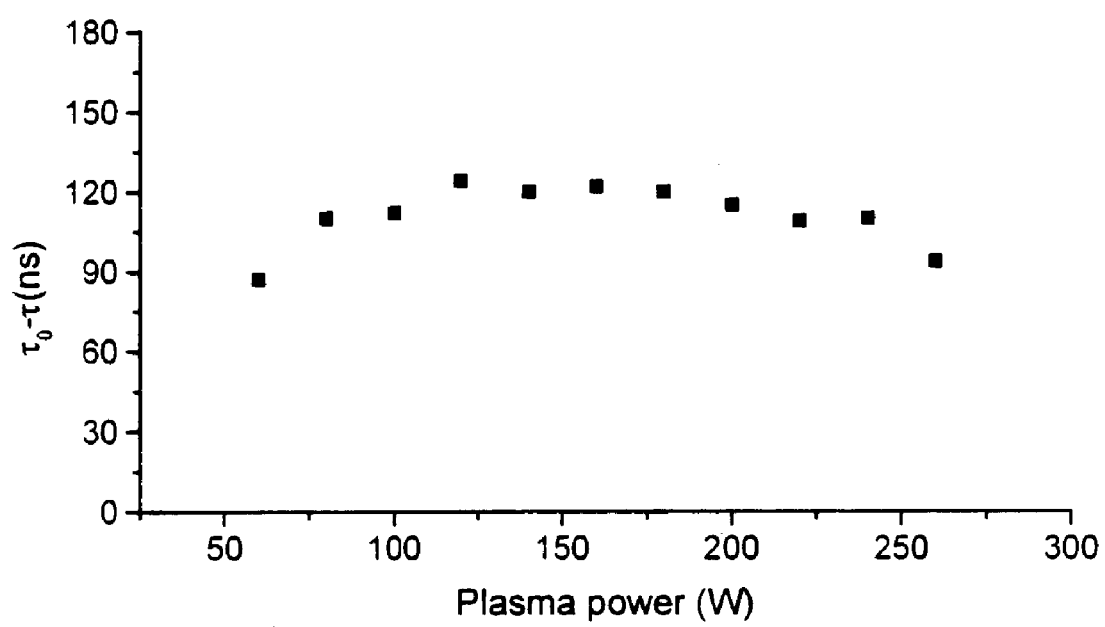
FIG. 2 is the microwave power influence on the signal intensity. Lead concentration: 100 ppb; Plasma observation height: 6 mm above the top of the torch; Plasma gas flow rate: 0.35 l/min; Carrier gas flow rate: 0.45 l/min; Other experimental conditions are the same as in Table 1.

(1) Plasma Power Influence. The plasma source can be operated from as low as 50 watts to about 300 watts, which is the highest power that can use with this particular power supply. In this wide range, as is shown in FIG. 2, the inventors found that the lead signal increases with microwave power increase at initial step from 50 to about 100 watts, and then the signal tends to level off from about 100 to 180 watts. Further increase of the power decreases the lead signal significantly. This hints that high power may benefit excitation and ionization states and may reduce atom populations in the ground state. In this point of view, a relatively low power is preferred for the atomic absorption measurement. A careful examination from the power influence in the range from 100 to 180 watts, the inventors found that 120 watts is probable the best value to use since the absorbance at this power is slightly higher than others, even not significant. For this reason, this power was chosen for all our subsequent work unless otherwise stated.

Figure 3:
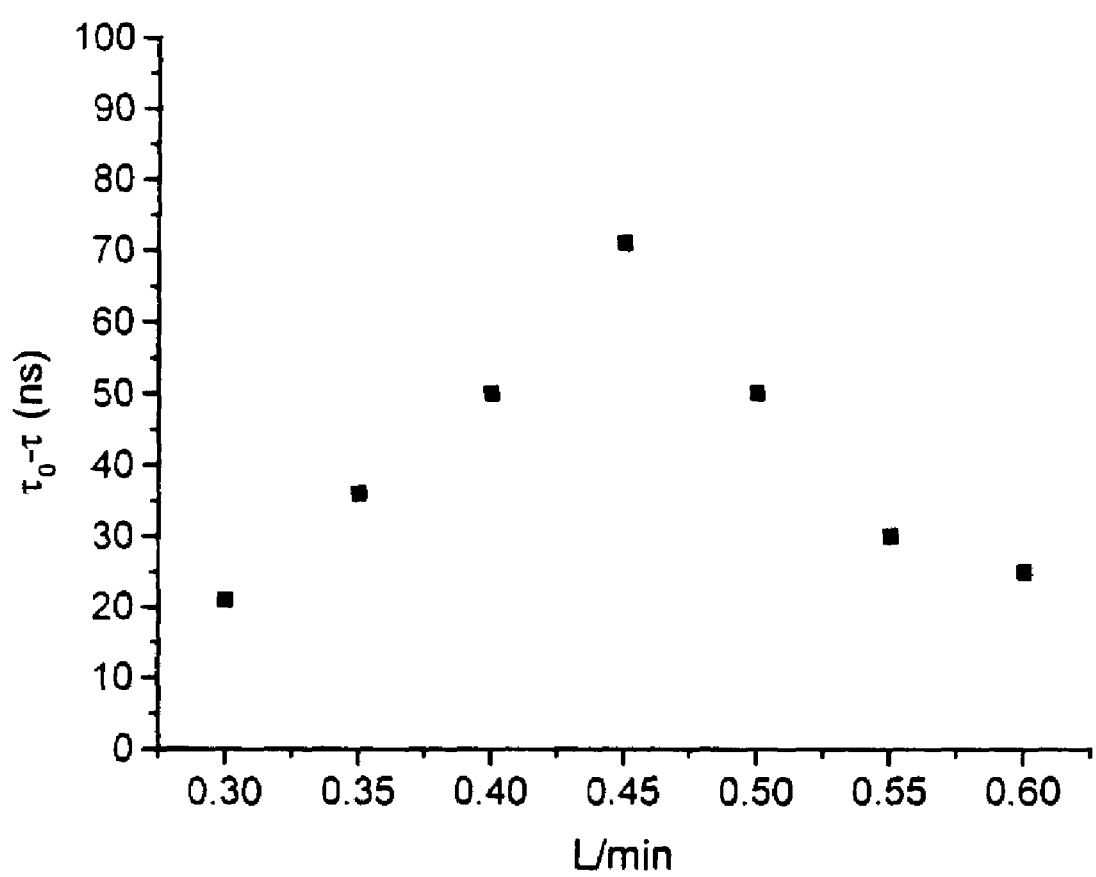
FIG. 3 is a sample carrier gas flow rate influence on lead signal intensity. Sample concentration: 100 ppb; Microwave power: 120 W; Other experimental conditions are the same as in FIG. 1.

(2) Carrier Gas Flow Rate. Another important parameter for system performance is carrier gas flow rate, which serves to bring samples into the plasma. Lower carrier gas flow rate is good for a longer analyte residence time but carries only less sample into the plasma, which is not favorite for absorption measurement. From this point of view, a higher carrier flow rate should be good for sampling more samples, however, if the flow rate is too high, it will significantly reduce the analyte residence time and therefore, decrease signal intensity. This phenomenon is well explained in FIG. 3, which gives an optimum value at about 0.45 L/min. From FIG. 3, it can also be seen that carrier gas flow rate is critical as the curve shape is pretty sharp, either before or after the maximum peak, which means that carefully control the flow rate is needed in order to obtain best sensitivity.

Figure 4:
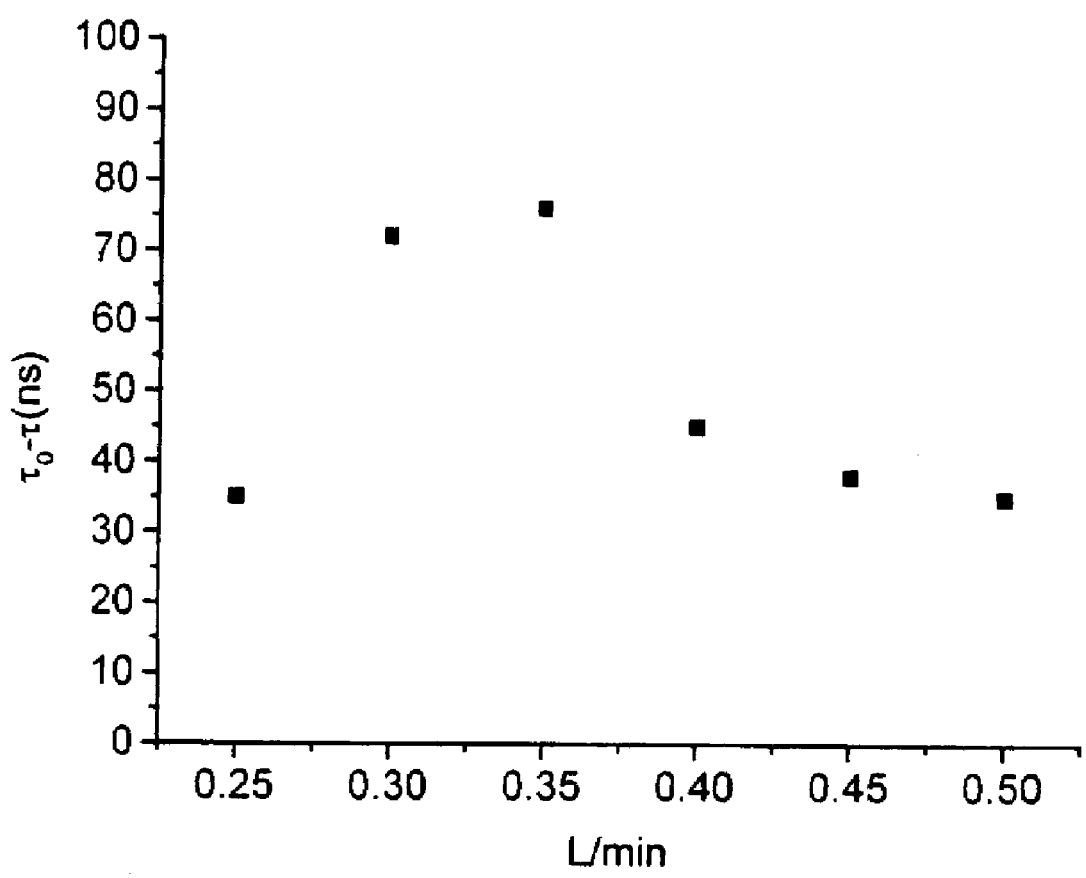
FIG. 4 is the plasma support gas flow rate influence on signal intensity. Experimental conditions are the same as in Table 1.

(3) Plasma Support Gas Flow Rate. The plasma support gas is critical for plasma running. A stable plasma usually needs a certain flow rate to run. Extra lower flow rate may cause plasma unstable and influence the system performance. FIG. 4 gives plasma support gas flow rate influence on the lead signal intensity. As is shown in the Figure, a maximum signal appears at a flow rate around 0.35 l/min. Further increase of plasma gas flow rate obviously decreases the signal. The asymmetric shape of the curve in FIG. 4 demonstrates that higher flow rate critically sharply lowers signal intensity when flow rate is over 0.35 l/min. This phenomenon can be explained that higher plasma support gas flow rate may influence the analyte concentration in the plasma through gas dilution of the analytes. For this reason, the inventors choose 0.35 l/min as optimum value for plasma support gas flow rate in further tests.

Figure 5:
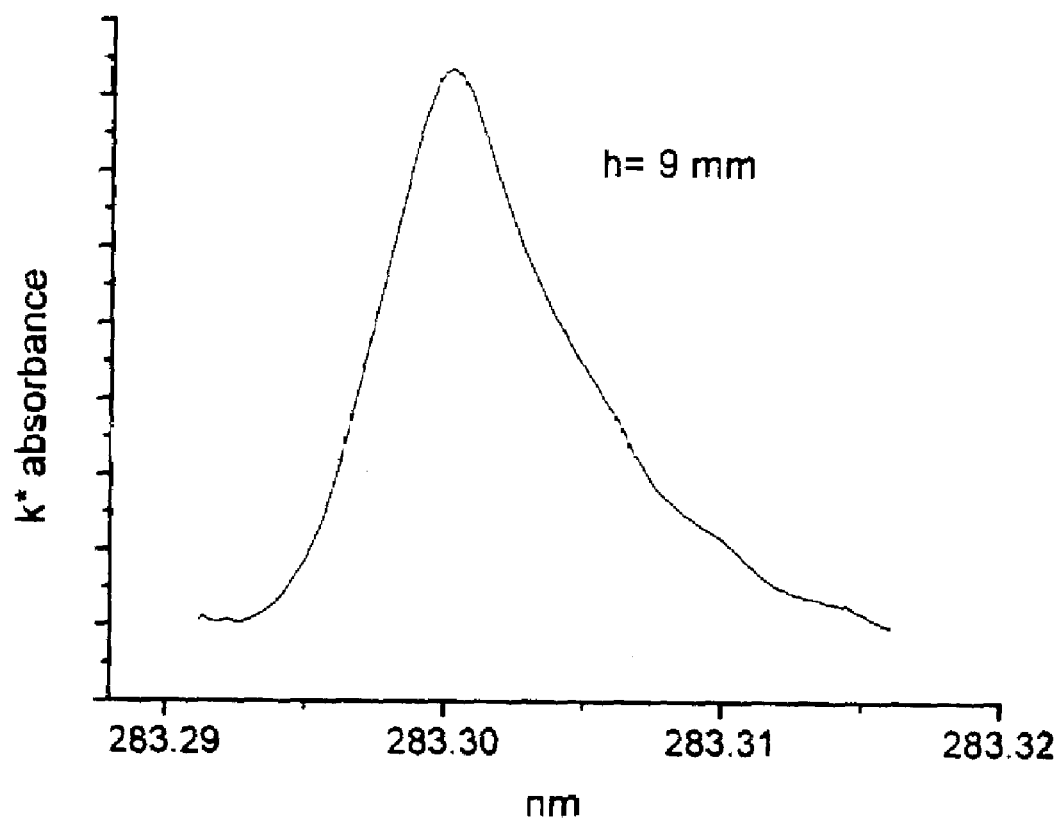
FIG. 5 is the lead line shape at 283.3 nm. Scan was performed at observation height of 9 mm through the center of the plasma source with a scan step of 0.0003 nm. Microwave power used: 120 W, Lead concentration: 250 ppb; All other experimental conditions are the same as in Table 1.

Analyte Line Shape. Lead line shapes were obtained at different observation heights through laser wavelength scan within a narrow wavelength range. FIG. 5 shows a typical line shape recorded through the center of plasma at observation heights of 9 mm. The measured absorbance was corrected using background absorption from a blank solution and normalized for comparison purpose. The scanning range for the lead line (283.3 nm) is about 0.03 nm, and the scanning step is 0.0003 nm. At each data point, 100 laser shots were averaged. A 3–5 point-smooth was applied to the data before plotting. It has been demonstrated that at lower observation positions, the plasma is more stable and the baseline noise is relatively smaller than that at higher positions. However, at each position, the baseline noise is significantly lower than that identified in ICP plasma source [12]. The recorded line widths are determined by both instrument and physical broadening [24, 25]. In this study, the instrument broadening comes from the laser line width (<0.65 pm) and the physical broadening mainly from Doppler and collisional broadenings, which yield Gaussian and Lorentzian line shapes, respectively. With all these broadening mechanisms and reactions, the lead line shape in FIG. 5 is of a Voigt profile [26]. Since the peak width at half height is usually used to evaluate the system resolution, an estimate was made in this work that the peak widths of lead at half height are around 7 to 8 pm, slightly depending on the observation positions, where Doppler and collisional broadenings are different.

Figure 6:
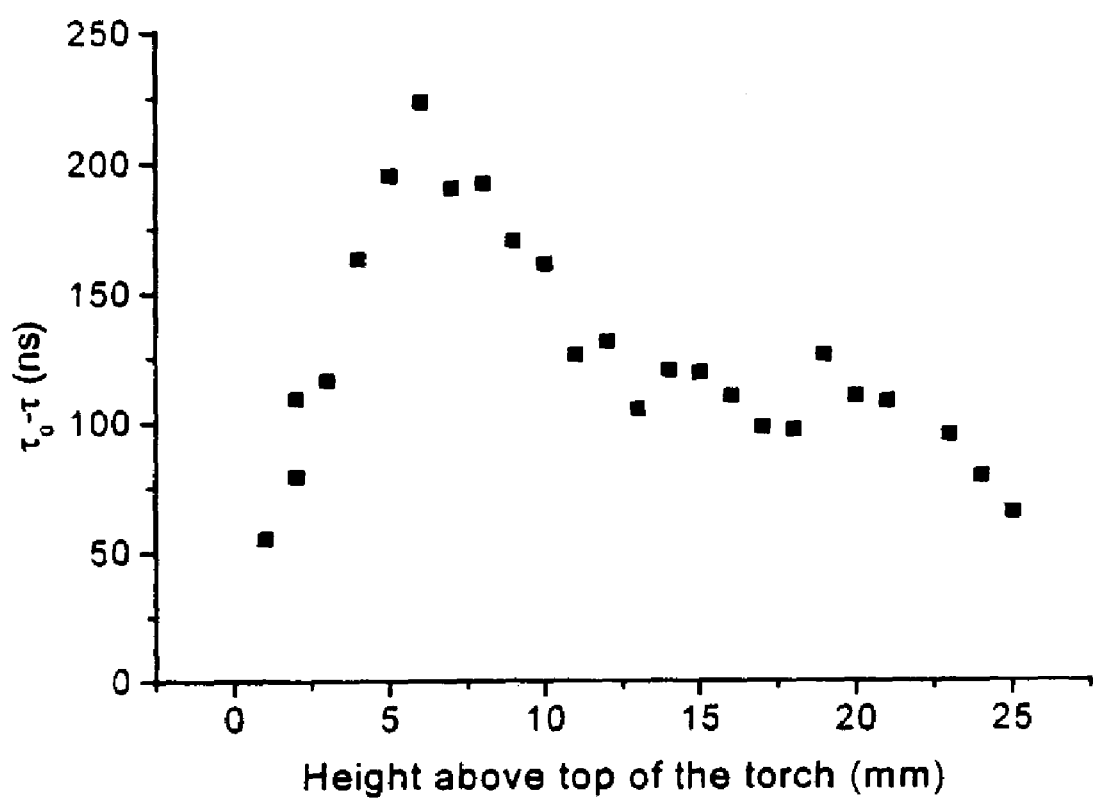
FIG. 6 is a vertical profile of analyte distribution— Observation height influence on analyte signal. Data points were collected along the center of the plasma with a step height of 1 mm for each point. Lead concentration: 250 ppb; Microwave power used: 100 W; Other experimental conditions are the same as in Table 1.

Vertical Profile of Analyte Distributions. Observation height is another important parameter for the system optimization. In this work, observation height influence on lead absorbance at 283.3 nm was thoroughly examined. Background corrections were made by subtracting the absorption profiles obtained with a blank solution (no lead). FIG. 6 shows the measured absorbance for lead 283.3 nm line versus observation height above the top of the torch. Each point on the curve results from an average of 20 signals with constant measurements. At the initial points of lower positions, the absorbance increases significantly with the observation height. The maximum signal was obtained around observation height of 6 mm, and after that, the absorbance decreases with the further increase of observation height. Interestingly, a close examination can identify that there are another two peaks in the analyte distribution at higher positions of about 14 mm and 19 mm, respectively (see FIG. 6). These results can be reasonably explained by the plasma shape, which consists of two major portions, an upside-down cone and a candle flame. There is an obvious cross point between these two portions and link them together. The results obtained in this work demonstrate that the highest density of ground states of analyte locates at height of about 6 mm above the top of the torch, corresponding to the first maximum absorbance peak in FIG. 6. The other two small peaks in the higher positions (14 mm and 19 mm) are located within the plasma tale plume, where the relatively cool environment makes significant recombination from ions and electrons happen. These findings obtained with microwave plasma source are significantly different from what reported in ICP source, in which whatever power used, the maximum absorbance is always located at the lowest possible position examined [12]. In addition, the significant absorption valley region in ICP source, which was identified due to higher degree of ionization of lead atoms [12], was not observed in this microwave plasma source. This result suggests that ionization process in the microwave plasma be less significant than in ICP source and microwave plasma can provide more ground state population for absorption measurement.

Figure 7:
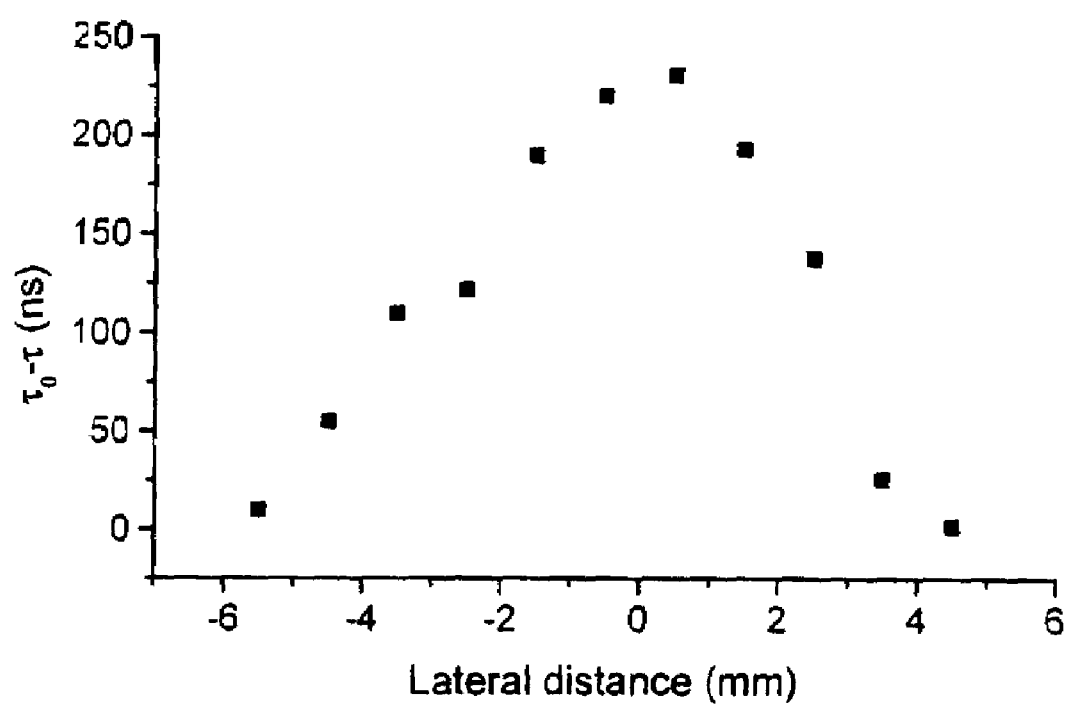
FIG. 7 is the lateral profile of analyte distribution. Data points were collected at observation height of 9 mm, with a step width of 1 mm for each point. Other experimental conditions are the same as in FIG. 6.

Lateral Analyte Distributions. As discussed above, the plasma source has two portions with a joint point between. Measurement of lateral analyte distributions at different observation heights will for sure result in different profiles. In this work, the observation height of 9 mm was selected as representative for our lateral profiling measurement. This particular position is just above the joint point and the plasma has a relative wide spread at this position. FIG. 7 shows the lead absorbance at 283.3 nm versus lateral position. Again, each point generated in the curve is the average of 20 signals. It seems that the analyte is uniformly diffused during the transportation process in the plasma, and a close symmetrical profile was obtained at this particular observation position. Although further exploration for the lateral analyte distribution is not pursued at this time, obviously, cavity ring-down spectroscopy is capable of mapping out the distributions of numerous species and electron population in the same manner [12].

Figure 8:
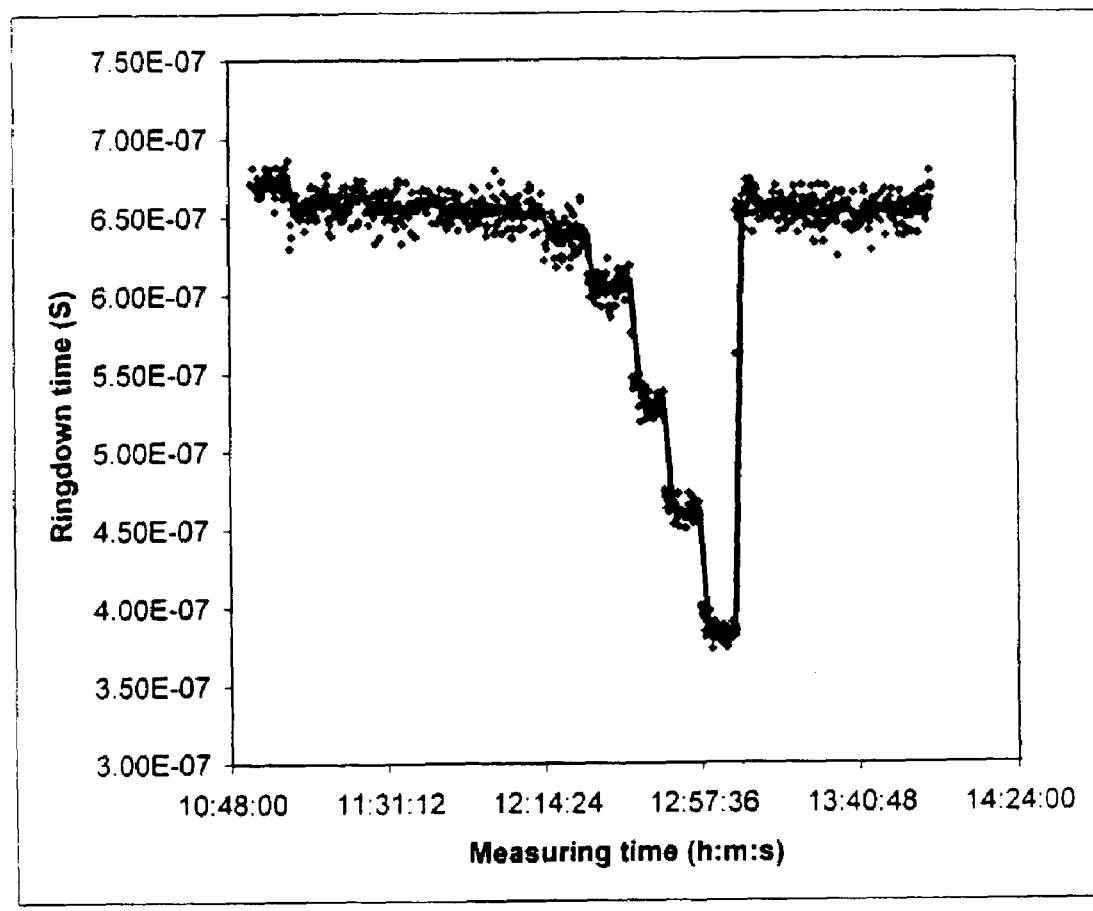
FIG. 8 is a cavity ring-down time versus analyte concentration. Analyte concentration range tested: 2.5–250 ppb; Experimental conditions are same as in Table 1.
Figure 9:
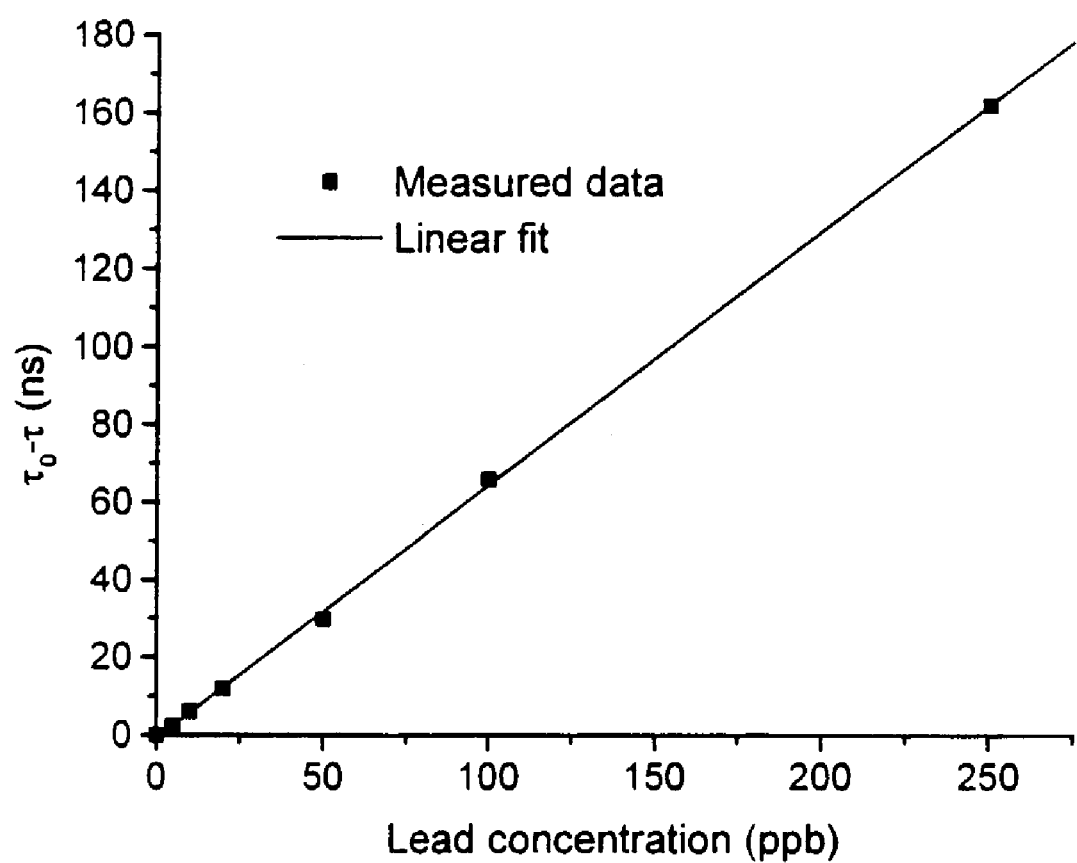
FIG. 9 is the calibration curve of lead obtained with microwave plasma source cavity ring-down spectroscopy. Experimental conditions are the same as in Table 1.

Analytical Figures of Merit. Since the present invention is the first time to successfully combine a microwave plasma source with cavity ring-down spectroscopy for elemental measurement, it is necessary to examine the analytical performance for the novel device. As an initial step, a rough examination was performed to show signals versus sample concentrations. As is shown in FIG. 8, the signal intensities are well response to the analyte concentrations, from about 250 ppb to as low as 2.5 ppb. Each step in the FIG. 8 represents one concentration. Even at concentration of 2.5 ppb, a measurable signal still can be obtained with this new instrument. FIG. 9 gives a calibration curve for the lead measurement. In the concentration range tested, a good linearity with a $R^2=0.9974$ was obtained for this work. With the optimized operating conditions, the ring-down time is 990 ns when the plasma is off, corresponding to an effective reflectivity of 99.72%. With the plasma on, the ring-down time drops to some extent based on the observation position used. Detection limit of lead is estimated based on the calibration curve in FIG. 9 and the baseline noise of the measurement. By using an average of 50 laser shots without further point-smooth applied, the baseline stability of about 0.3% is obtained with this microwave plasma source. Based on the $3\sigma$ defined for calculation of limit of detection (LoD), the experimental measurement of LoD is 0.8 ng/ml. On the other hand, the detection limit can also be theoretically calculated based on equation (2), given the calculated absorption cross-section of the element, effective absorption path length (1~3 mm) of the plasma source, and an estimated nebulizer efficiency of 7%, mirror effective reflectivity of 99.72%, and the baseline noise of 0.3% [12]. According to these parameters, the theoretical LoD of lead for the instrument device is about 0.2 ng/ml. Note that a deliberately pursue of the detection limits were not performed at this time. With a systematic optimization of the system operating conditions, combined with higher reflective mirrors and single mode laser sources, the detection limit can be significantly improved.

Figure 10:
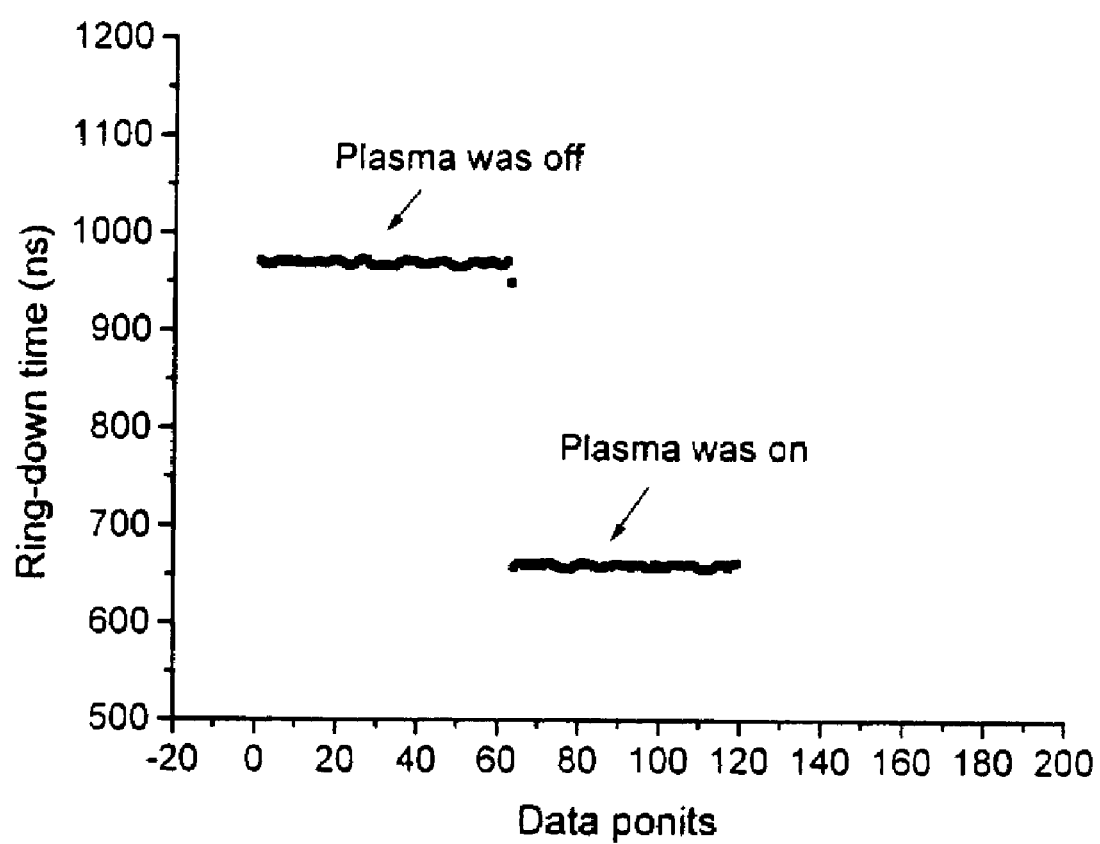
FIG. 10 is the noise comparison with and without plasma source. Up baseline obtained with plasma source off condition and down baseline obtained with plasma source on condition. Experimental conditions are the same as in Table 1.

Plasma Noise and Limitations. Plasma stability has a large bearing on the system limitation of measurements. Plasma, as the gas cell located within the ring-down cavity, brings additional noise source into the system. The baseline noise is defined by standard derivation divided by ring-down time, namely, $\sigma/\tau$ [12]. In a pulsed ICP-CRDS system [12], the inventors found that baseline noise is 3 to 4 times larger when plasma is on than that when plasma is off. The typical baseline noise is 0.3% when plasma is off and 0.8~1.2% when plasma is on. This means ICP plasma stability is a dominant source of baseline noise, compared with optical and electronic noises, which are contributed by laser shot-to-shot noise, mode match, Fabry-Perot effect [27], detector dark current noise, and digital resolution noise [28]. When working with the pulsed laser microwave plasma CRDS system, the inventors found that the plasma did not generate additional baseline noise to the system. Plasma on or off has no effect at all on the baseline noise, except for the decrease of ring-down time resulting from the addition of scattering loss. This interesting finding encourages us to further explore the potential of microwave plasma source for ring-down measurements. FIG. 10 shows the comparison of baseline noise levels when the microwave plasma on and off. Baseline noise levels in both situations are same at about 0.3%, which was only determined by the system optical and electric noises. These results indicate that the baseline noise was improved by a factor of 3~4 through using microwave plasma to replace ICP source. By rearranging Equation (2) in Section 3, the absorbance equation is:

$$\text{Absorbance} = \sigma n d = (1-R)\frac{\Delta\tau}{\tau} \quad (3)$$

Where, $\sigma$, n, d, and R are as defined in Equation (1); $\tau$ is the ring-down time with analytes, and $\Delta\tau$ is the difference between $\tau_0$ (without analytes) and $\tau$. Equation (3) clearly indicates that for a given mirror reflectivity, the minimum detectable absorbance of the system depends completely upon the baseline noise, $$\frac{\Delta\tau}{\tau},$$

here $\Delta\tau\rightarrow\sigma$.

Based on this consideration, the microwave plasma source provides additional space to improve the system directivity. Compared with ICP plasmas, microwave plasmas have more flexibility in discharge designs so that one can increase absorption path length without sacrificing the desired baseline stability. A prolonged linear microwave plasma coupled with state-of-art physical configuration of CRDS device can certainly significantly improve system detection capability by orders of magnitude.

Conclusion

The present invention successfully combines a microwave plasma source with cavity ring-down spectroscopy. The combination of CRDS and microwave plasma source provides a novel system that offers unexpected advantages over the conventional devices and methods. For example, CRDS possesses extremely sensitive absorption measurement capabilities ($<10^{-6}$ per pass fractional absorption) and offers high resolution when combined with the narrow linewidth lasers. With a single laser pulse ringing down inside the cavity over a thousand times, CRDS is usually thousand times more sensitive than conventional absorption techniques. Furthermore, the low pulse energy coupled into the cavity in plasma source CRDS avoids saturation effects, which have long been known to be an issue for laser atomic absorption. The linearity of the calibration curves obtained for lead also indicates a lack of saturation effects in CRDS for trace concentrations. Compared with conventional inductively coupled plasma (ICP) sources, a microwave plasma source possesses advantages of low power, low plasma gas flow rate, and the ability sustained with various gases. All of these characteristics of the present invention are highly superior over conventional art devices and methods for atomic absorption measurements due to the larger fractional atom population in the ground energy level, the lower ionization fraction in the plasma source, and the longer residence time of free atoms within the plasma. In addition, the microwave plasma source coupled with CRDS can bring better ring-down baseline stability, provide more flexible design favorable for absorption measurement, and have significant mass reduction in instrument design and fabrication. The inventor's discovery of microwave plasma source cavity ring-down spectroscopy provide a novel tool for highly sensitive elemental determination and hyperfine structure analysis.

LITERATURE CITED

1. A. Montaser and D. W. Golightly, Inductively Coupled Plasma in Analytical Atomic Spectrometry, [VCH Publishers, Inc. 1992].
2. Houk R. S., Anal. Chem., 1986, 58, 97A.
3. J. D. Ingle Jr. and S. R. Crouch, Spectrochemical Analysis, Prentice-Hall Inc., New Jersey, 1988, P 300.
4. W. J. Price, Spectrochemical Analysis by Atomic Absorption, John Wiley & Sons, New York, 1985.
5. R. H. Wendt and V. A. Fassel, Anal. Chem., 38, 377(1966)
6. C. Vellion and M. Margoshes, Spectrochim. Acta., 23B 509(1968)
7. B. Magyer and F. Aeschbach, Spectrochim. Acta., 31B, 483(1980)
8. L. P. Hart, B. W. Smith, N. Omenetto, Spectrochim. Acta, 41 B, 1367(1986).
9. G. Gillson, G. Horlick, Spectrochim. Acta, 41B, 431 (1986).
10. M. A. Mignardi, B. W. Smith and J. D. Winefordner, Anal. Chem., 62, 586(1990)
11. G. P. Miller and C. B. Winstead, J. Anal. Atomic Spectro. 12, 907 (1997).
12. C. Wang, F. J. Mazzotti, G. P. Miller, and C. B. Winstead, Appl. Spec. 56, 386 (2002).
13. C. B. Winstead, F. J. Mazzotti, J. Mierzwa and G. P. Miller, Anal. Commun. 36, 277 (1999).
14. Q. Jin, Y. Duan, and J. A. Olivares, Spectrochim. Acta 52B, 131, 1997.
15. Y. Duan, M. Huo, Z. Du and Q. Jin, Appl. Spectrosc., 47, 1871, 1993.
16. Ng, K. C.; and Garner, T. G., Appl. Spectrosc., 1993, 47, 241.
17. Y. Duan, X. Li and Q. Jin, J. Anal. At. Spectrom., 8, 1091, 1993.
18. Y. Duan, H. Zhang, M. Huo and Q. Jin, Spectrochim. Acta, 49B (6), 583, 1994.
19. Y. Duan, M. Huo, J. Liu and Q. Jin, F. J. Anal. Chem., 349, 277, 1994.
20. Y. Duan, Y. Su, Z. Jin, S. Abeln, S. Rev. of Sci. Instru. 71, 1557, 2000.
21. Jin, Q.; Zhu, C.; Borer, M. W.; Hieftje, G. M. Spectrochim. Acta. 1991, 46B, 417–430.
22. Y. Duan, Y. Su, Z. Jin, and S. P. Abeln, Anal. Chem., 72, 1672, 2000.
23. A. O'Keefe and D. A. G. Deacon, Rev. Sci. Instrum. 59 (12), 2544–2551 (1988).
24. P. W. J. M. Boumans and J. J. A. M. Vrakking, Spectrochim. Acta 41B, 1235 (1986).
25. A. C. G. Mitchell and M. W. Zemansky, Resonance Radiation and Excited Atoms, Cambridge University Press, Cambridge 1934.
26. R. G. Breene, The shift and Shape of Spectral Lines, Pergamon Press, Oxford, 1961.
27. Chuji Wang, et al. Unpublished test results of MTO-1000-H20, Tiger Optics LLC.
28. R. D. van Zee, J. T. Houdges and J. P. Looney, Applied Optics, Vol. 38, No. 18, 3951 (1999).

What is claimed is:

1. A system for highly sensitive measurements of elements and isotopes, comprising:
   a microwave plasma source, and
   a cavity ring-down spectroscopy system comprising:
   an optical cavity; and
   a laser producing a laser beam,
   wherein said microwave plasma source is operationally connected to said cavity ring-down spectroscopy system and provides a microwave induced plasma as an atomic source for said cavity ring-down spectroscopy system.
2. The system of claim 1, further comprising a photomultiplier tube or photodiode detector for monitoring ring-down signals.
3. The system of claim 2, further comprising a digital oscilloscope interfaced to a computing device for recording said ring-down signals.
4. The system of claim 3, wherein a detection limit as low as 0.8 ppb ($10^{-10}$) can be obtained.
5. The system of claim 4, wherein said laser is a tunable dye laser or continuous wave diode laser.
6. The system of claim 5, wherein said laser provides a single laser pulse ringing down inside said cavity ring-down spectroscopy system.
7. The system of claim 3, further comprising a spatial filter system for mode matching said laser beam to said ring-down cavity spectroscopy system.
8. The system of claim 7, wherein said laser beam is a Pseudo-Gaussian beam.
9. The system of claim 3, further comprising an interference filter mounted in front of the photomultiplier tube to reject emissions from said microwave plasma.
10. The system of claim 3, further comprising a pulse generator for controlling the timing of said system operation.
11. The system of claim 3, wherein said microwave plasma source provides said microwave plasma with a power between about 50 to 1,000 watts.
12. The system of claim 3, wherein said microwave plasma source is connected to a microwave plasma torch, said plasma torch being mounted inside said optical cavity.
13. The system of claim 12, further comprising a three-dimensional adjustable stage for mounting said microwave plasma torch,
   wherein said beam can be precisely aligned to maximize absorption.
14. The system of claim 13, further comprising:
   a nebulizer for aerosol formation of samples in solvent prior to introduction into said system, and
   a pump for providing said samples into said system.
15. The system of claim 1, wherein said plasma source is a low power microwave plasma source.
16. A method for measuring elements and isotopes, said method comprising:
   providing a system, which comprises a microwave plasma source, a cavity ring-down spectroscopy system having an optical cavity and a laser for producing a laser beam, a photomultiplier tube for monitoring ring-down signals, and a digital oscilloscope interfaced to a computing device for recording and analyzing said ring-down signals, wherein said microwave plasma source is operationally connected to said cavity ring-down spectroscopy system and provides a microwave induced plasma as an atomic source for said cavity ring-down spectroscopy system;
   introducing a sample into said system, and
   obtaining a measurement analysis from said computing device.
17. The method of claim 16, wherein said sample is combined with a solvent and provided to said system as an aerosol.

* * * * *